United States Patent
Curiel et al.

(10) Patent No.: US 9,498,303 B2
(45) Date of Patent: Nov. 22, 2016

(54) ASSEMBLY FORMED BY A SELF-LIGATING BRACKET AND AN ELASTIC CLIP, FOR AN ORTHODONTIC APPARATUS

(75) Inventors: Patrick Curiel, Neuilly sur Seine (FR); Philippe Salah, Paris (FR); William Ayache, Neuilly sur Seine (FR)

(73) Assignee: H32, Paris (FR)

( * ) Notice: Subject to any disclaimer, the term of this patent is extended or adjusted under 35 U.S.C. 154(b) by 0 days.

(21) Appl. No.: 13/997,559

(22) PCT Filed: Dec. 27, 2011

(86) PCT No.: PCT/EP2011/074098
§ 371 (c)(1),
(2), (4) Date: Sep. 3, 2013

(87) PCT Pub. No.: WO2012/089735
PCT Pub. Date: Jul. 5, 2012

(65) Prior Publication Data
US 2013/0337399 A1   Dec. 19, 2013

(30) Foreign Application Priority Data
Dec. 28, 2010  (FR) ...................... 10 61312

(51) Int. Cl.
*A61C 7/30*  (2006.01)
*A61C 7/28*  (2006.01)

(52) U.S. Cl.
CPC *A61C 7/30* (2013.01); *A61C 7/285* (2013.01)

(58) Field of Classification Search
CPC .............................. A61C 7/285; A61C 7/287
USPC ...................................................... 433/10, 11
See application file for complete search history.

(56) References Cited

U.S. PATENT DOCUMENTS

| 4,248,588 | A | * | 2/1981 | Hanson ........................... 433/11 |
| 4,419,078 | A | * | 12/1983 | Pletcher ........................... 433/10 |
| 5,474,445 | A | | 12/1995 | Voudouris |
| 5,562,444 | A | | 10/1996 | Heiser et al. |
| 5,630,715 | A | | 5/1997 | Voudouris |

(Continued)

FOREIGN PATENT DOCUMENTS

| DE | 4407100 A1 | 9/1995 |
| EP | 1234549 A1 | 8/2002 |

(Continued)

OTHER PUBLICATIONS

International Search Report, PCT International Application No. PCT/EP2011/074098, mailed Mar. 6, 2012.
Office Action issued in corresponding FR No. 10 61312, mailed Aug. 23, 2013.

*Primary Examiner* — Ralph Lewis
(74) *Attorney, Agent, or Firm* — Andrus Intellectual Property Law, LLP (57) ABSTRACT

An assembly of a self-ligating bracket intended to be part of an orthodontic apparatus. The bracket having in the longitudinal direction thereof an outer face and an occlusal face and being provided on the outer face thereof with a groove for holding an orthodontic arch wire. An elastic clip that can be moved in a reversible manner between an open position, leaving a free passage for the insertion of the arch wire into the groove or the extraction of the arch wire from the groove, and a closed position closing off the groove. The clip being moveable between said positions by a rotational movement, without the clip sliding in translation.

19 Claims, 8 Drawing Sheets

(56) References Cited

U.S. PATENT DOCUMENTS

| | | | |
|---|---|---|---|
| 5,711,666 A | 1/1998 | Hanson | |
| 5,857,850 A | 1/1999 | Voudouris | |
| 5,906,486 A * | 5/1999 | Hanson | 433/11 |
| 5,913,680 A | 6/1999 | Voudouris | |
| 6,071,118 A | 6/2000 | Damon | |
| 6,071,119 A | 6/2000 | Christoff | |
| 6,168,428 B1 | 1/2001 | Voudouris | |
| 6,257,883 B1 | 7/2001 | Voudouris | |
| 6,368,105 B1 | 4/2002 | Voudouris et al. | |
| 6,939,133 B2 | 9/2005 | Voudouris | |
| 7,104,791 B2 * | 9/2006 | Hanson | 433/10 |
| 7,214,057 B2 | 5/2007 | Voudouris | |
| 7,247,019 B2 | 7/2007 | Abels et al. | |
| 7,416,408 B2 | 8/2008 | Farzin-Nia et al. | |
| 7,442,039 B2 * | 10/2008 | Opin et al. | 433/11 |
| 7,611,353 B2 | 11/2009 | Sommer | |
| 7,963,767 B2 | 6/2011 | Lewis et al. | |
| 7,967,603 B2 * | 6/2011 | Heiser | A61C 7/285 433/10 |
| 2004/0166459 A1 | 8/2004 | Voudouris | |
| 2004/0175667 A1 | 9/2004 | Abels et al. | |
| 2007/0072143 A1 | 3/2007 | Sommer | |
| 2007/0166658 A1 | 7/2007 | Voudouris | |
| 2009/0004617 A1 | 1/2009 | Oda et al. | |
| 2010/0261131 A1 | 10/2010 | Ruiz-Vela et al. | |

FOREIGN PATENT DOCUMENTS

| | | |
|---|---|---|
| EP | 1287789 A2 | 3/2003 |
| WO | 2008044912 A1 | 4/2008 |
| WO | 2010028276 A1 | 3/2010 |
| WO | 2010103178 A1 | 9/2010 |

\* cited by examiner

ASSEMBLY FORMED BY A SELF-LIGATING BRACKET AND AN ELASTIC CLIP, FOR AN ORTHODONTIC APPARATUS

CROSS-REFERENCE TO RELATED APPLICATIONS

This application is the U.S. national stage application of International Application PCT/EP2011/074098, filed Dec. 27, 2011, which international application was published on Jul. 5, 2012, as International Publication WO 2012/089735 in the French language. The International Application claims priority of French Patent Application 1061312, filed Dec. 28, 2010.

BACKGROUND

The invention relates to a base/bracket assembly to be used in a customized orthodontic apparatus for treating a patient and intended mainly, but not exclusively, to be used in the case of a lingual technique, that is to say with the apparatus located on the non-visible posterior face of the teeth.

Conventionally, such apparatuses comprise:
at least one orthodontic arch wire, in other words a metal wire which exerts on the teeth a force that tends to move them from their unsatisfactory initial position, known as the "malposition", into a satisfactory final position, known as the "corrected position";
and a set of brackets which are each provided with at least one groove for holding an orthodontic arch wire.

The brackets are fixed individually to the patient's teeth in a predetermined position that allows the orthodontic arch wire to transfer to the teeth the necessary forces for them to pass from the malposition into the corrected position during the treatment. This fixing is produced by way of a "base", that is to say an intermediate element, one face of which conforms to the surface of the tooth to which the bracket is intended to be fixed, and the other face of which supports the bracket.

Most commonly, one or more orthodontic arch wires, together with a single set of brackets each comprising one or more grooves, are used.

The development of lingual orthodontic techniques, which have the esthetic advantage of leaving the apparatus virtually invisible from the outside, started around 1980. In these techniques, an important element in the success of the treatment is the good positioning of the bracket and of its groove on the tooth, since this positioning determines the orientation of the forces that are imposed on the corresponding tooth and thus the orientation of the tooth in the various spatial directions when it is located in the final corrected position. This positioning is much more difficult to carry out in the lingual technique than in the technique known as labial or vestibular (in which the apparatus is located or the anterior face of the teeth) on account of the great angulation of the posterior faces of the teeth. This angulation means that a small error in the positioning of the bracket can place the groove in an incorrect position which is incapable of correcting the position of the tooth as desired.

IT techniques have been able to bring significant improvements to the ease of designing customized orthodontic apparatuses that are specific to each patient.

In particular, document WO-A-03/068099 teaches designing in a customized manner an assembly formed firstly by the virtual image of a base for fixing to the tooth, designed digitally on the basis of a computer image of the patient's arch with the malpositioned teeth, and secondly by a virtual image of a bracket provided with a groove for the insertion of the orthodontic arch wire, this image being drawn from a virtual library of brackets having predetermined forms. Next, a bracket formed of a single body resulting from the combination of these two images is produced by rapid prototyping. Next, an orthodontic arch wire that is shaped with the aid of a special device and is intended to connect the brackets and to bring the patient's teeth into the corrected position is designed.

Once the orthodontic arch wire has been inserted into the groove in the bracket, this groove is closed off by the practitioner so as to keep the arch wire there. Most commonly, this closing off is realized by inserting a metal or elastomeric ligature into the groove. However, this method has the drawback of not having optimum reliability on account of the fact that it is possible for the ligature not to be fitted correctly by the practitioner and its properties can change over time, in particular in the case of an elastomeric ligature. If the ligature is displaced or damaged, the patient has to go to the orthodontist's practice in order to have it replaced. Likewise, the careful realization of each ligature takes a great deal of time, and this makes the fitting of the arch wire a lengthy and uncomfortable procedure for the patient. Finally, if, during the course of the treatment, it is necessary to change the arch wire, the orthodontist has to irreversibly destroy the ligatures in order to remove the arch wire, this procedure also being lengthy and uncomfortable for the patient. This step of destroying the ligature also causes the orthodontist to exert forces that are transmitted to the bracket and can weaken its connection to the base.

Considerable progress has been made by using what are known as "self-ligating" brackets. These brackets are designed to hold an elastic (metal) clip which, once the arch wire has been inserted, is placed in a position which closes off the groove and allows the clip to prevent the arch wire from coming out. This placement is generally carried out by sliding the clip in the longitudinal direction of the bracket between a stand-by position leaving the groove open for the insertion of the arch wire and a closed functional position closing off the groove, it being possible for this sliding to be complemented by a rotational movement as in document U.S. Pat. No. 6,776,613. The clip is moved manually by the orthodontist using one of his usual tools and takes only a fraction of a second. Similarly, the disengagement of the clip prior to changing the arch wire is carried out by simply pulling in the opposite direction to the previous sliding and is just as quick. Finally, the mechanical and dimensional characteristics of the metal clip are stable over time and if the bracket and the clip are produced with good dimensional precision, the functionality and reliability of the ligature are satisfactory.

However, the known self-ligating brackets also have their drawbacks. They are often more bulky than ordinary brackets on account of the fact that the longitudinal sliding movement of the clip has to be able to take place over a certain travel. Above all, this sliding movement can be hampered if tartar has built up on the bracket because it has not been removed by proper brushing of the apparatus in the mouth by the patient. When the arch wire is changed, the opening and replacement of the clip are thus made more difficult and one of the advantages of self-ligating brackets is at least partially lost.

BRIEF DISCLOSURE

The aim of the invention is to provide orthodontists with a device for connecting a tooth and an orthodontic arch wire, comprising a self-ligating bracket and its associated clip, and limiting or doing away with the abovementioned drawbacks.

To this end, one subject of the invention is an assembly formed by:

a self-ligating bracket intended to be part of an orthodontic apparatus, said bracket having in its longitudinal direction an outer face and an occlusal face and being provided on its outer face with a groove for holding an orthodontic arch wire;

and an elastic clip that can be moved in a reversible manner between an open position, leaving a free passage for the insertion of the arch wire into the groove or the extraction of the arch wire from the groove, and a closed position closing off the groove;

characterized in that said bracket and said clip comprise means allowing the clip to be moved between said positions substantially by a rotational movement, without the clip sliding in translation.

The clip may be generally U-shaped, with an end of a first arm, which closes off the groove in the bracket, being held in a first housing formed on the outer face of the bracket, and with an end of a second arm being held in a second housing formed on the occlusal face of the bracket.

The clip may comprise at least four successive parts, a first part, constituting a first terminal part of the clip, forming a tongue of width 11, intended to plunge into said first housing of the bracket, a second part of width 12, to which the first part is attached, intended to close off the groove in the bracket when the clip is in place, a third part of width 13 constituting an elastic junction between, on the one hand, the second part and, on the other hand, a fourth part of width 14, constituting a second terminal part of the clip and forming a tab intended to be inserted into the second housing of the bracket to manage the rotation of the clip during its movements commanded by the orthodontist.

The width 11 of the first part of the clip may be less than the width 12 of the second part of the clip.

The width 13 of the third part of the clip may be less than the width 12 of the second part of the clip.

The width 14 of the fourth part of the clip may be greater than the width 13 of the third part of the clip.

The clip may comprise a grasping means enabling the practitioner to move it between said positions.

Said grasping means may be an orifice formed on said second part of the clip.

Another subject of the invention is an assembly formed by:

a self-ligating bracket intended to be part of an orthodontic apparatus, said bracket having an outer face and an occlusal face and being provided on its outer face with a groove for holding an orthodontic arch wire;

an elastic clip that can be moved between an open position, leaving a free passage for the insertion of the arch wire into the groove or the extraction of the arch wire from the groove, and a closed position closing off the groove, the clip being generally U-shaped, with a first arm, which closes off the groove in the bracket, being held in a first housing formed on the outer face of the bracket, and with the end of a second arm being held in a housing formed on the occlusal face of the bracket;

and a base having an outer face and an occlusal face, said outer face of the base supporting said bracket and said occlusal face being intended to rest on a patient's tooth by conforming to the surface of said tooth, said base carrying on its outer face a wall that delimits, together with the occlusal face of the bracket, the housing in which the end of the second arm of the clip is held.

Said base may have on its outer face a support on which said bracket is placed.

Said support may comprise a housing in which said bracket is placed.

Another subject of the invention is a use of the assembly in an orthodontic apparatus of the lingual type.

Another subject of the invention is a use of the assembly in an orthodontic apparatus of the vestibular type.

Another subject of the invention is an orthodontic apparatus comprising an orthodontic arch wire and assemblies which each comprise a bracket, a clip and a base that are each intended to be fitted to a patient's tooth, characterized in that at least one of said assemblies is of the above type.

As will have been understood, the invention is based on a novel design of the assembly formed by a self-ligating bracket and the clip which closes off its groove. This assembly has a design which allows the clip to perform, during the closing and opening of the groove in the bracket, a movement which is practically a purely rotational movement. The previously usual sliding movement of the clip which could be hampered or prevented by a build-up of tartar on the path of the clip and complicated the removal of the orthodontic arch wire is thus done away with. It is also possible to give the bracket a more compact configuration, for example in its longitudinal direction, since the clip no longer slides as it passes from one position to the other. Even though the sliding travel has conventionally an apparently shorter length (around several tenths of a mm), in use this shortening of the bracket proves nevertheless to provide very appreciable extra comfort for the patient, especially if the apparatus is of the lingual type, as in the preferred (but not exclusive) application of the invention.

Another very significant advantage is that in the case of a build-up of tartar on the bracket, the clip remains easy to open since during the rotation the orthodontist has a sufficiently large lever arm to detach the layer of tartar.

Preferably, as in the preferred example described, the base which secures the bracket to the tooth is involved in fixing the clip to the bracket and in imposing its rotational movement.

BRIEF DESCRIPTION OF THE DRAWINGS

The invention will be understood better from reading the following description, which is given with reference to the following appended figures, in which.

DETAILED DISCLOSURE

This description will be given by taking as example the case in which the apparatus for which the bracket-clip-base assembly of the invention is intended is an apparatus of the lingual type. However, it will be obvious for a person skilled in the art to transpose the description to an assembly intended for an apparatus of the vestibular type.

Figure 1:
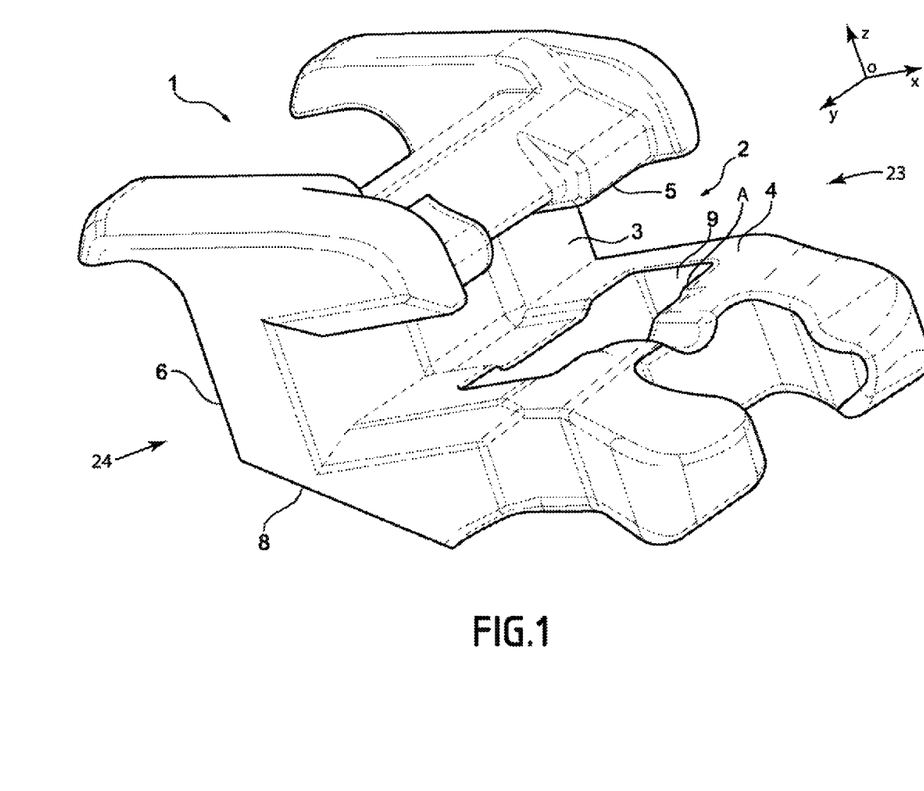
FIGS. 1 and 2 show a perspective view from the front and the rear of an example of a bracket according to the invention and intended for an orthodontic apparatus of the lingual type.
Figure 2:
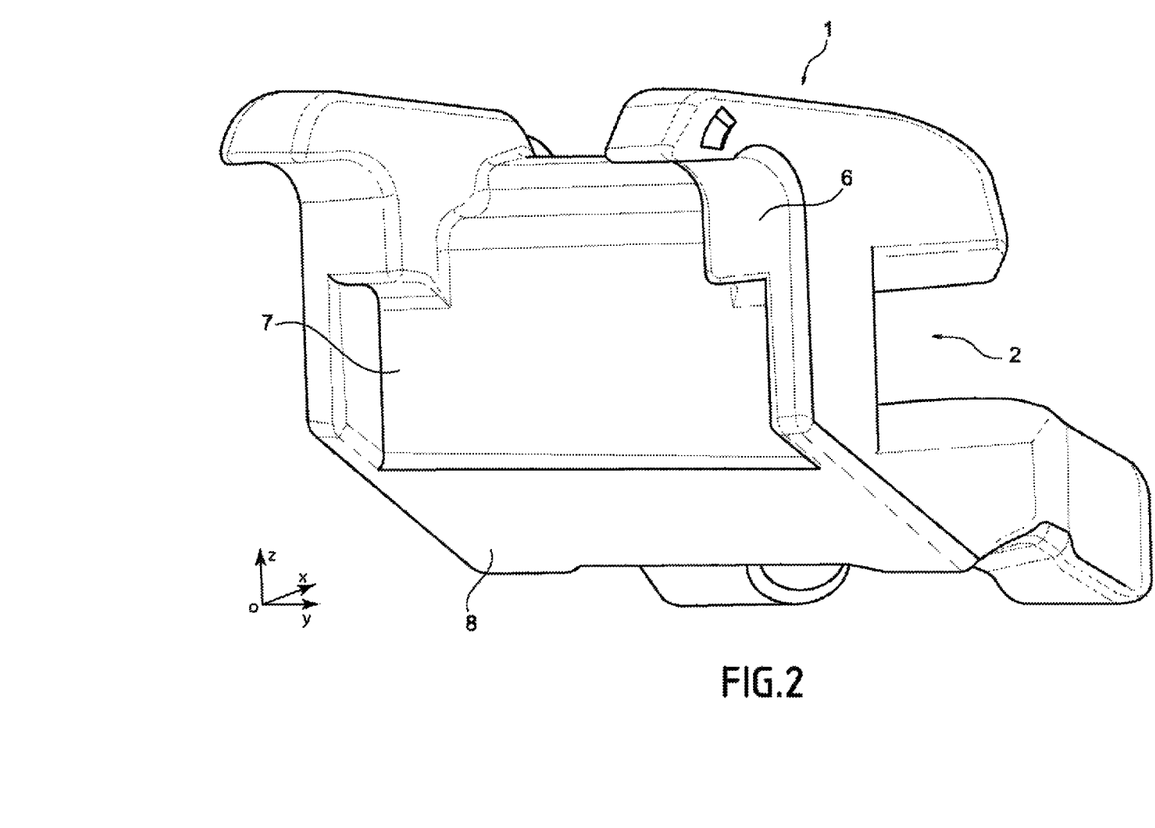

The bracket 1, which is shown in isolation in FIGS. 1 and 2, and of which the precise configuration shown is merely a nonlimiting example, comprises, with reference to the reference frame (O, X, Y, Z) shown in these same figures:

- a groove 2 of approximately C-shaped section open in the direction facing toward the patient's mouth (lingual direction), i.e. located on an outer face 23 of the bracket intended to receive an orthodontic arch wire, and delimited by an end wall 3 oriented approximately on the axes OY, i.e. the transverse axis of the bracket 1, and OZ, the axis perpendicular to the longitudinal direction OX of the bracket 1, and by two walls 4, 5 approximately perpendicular to the end wall 3 and forming the two arms of the C. These walls 4, 5 are oriented approximately on the axes OX and OY;
- a rear wall 6 situated on an occlusal face 24 of the bracket 1 which is intended to be directed toward the patient's tooth to which the bracket will be fitted, opposite the outer face 23. The rear wall 6 includes a housing 7 which is approximately rectangular in the example shown and the function of which will be seen hereinbelow;
- a planar base wall 8 which is intended to rest against the base which will carry the bracket 1.

The wall 4 delimiting the groove 2 and situated closest to the base wall 8 carries a housing 9 which is oriented mainly along the transverse axis OY of the bracket 1, and the function of which will be explained hereinbelow.

Figure 3:
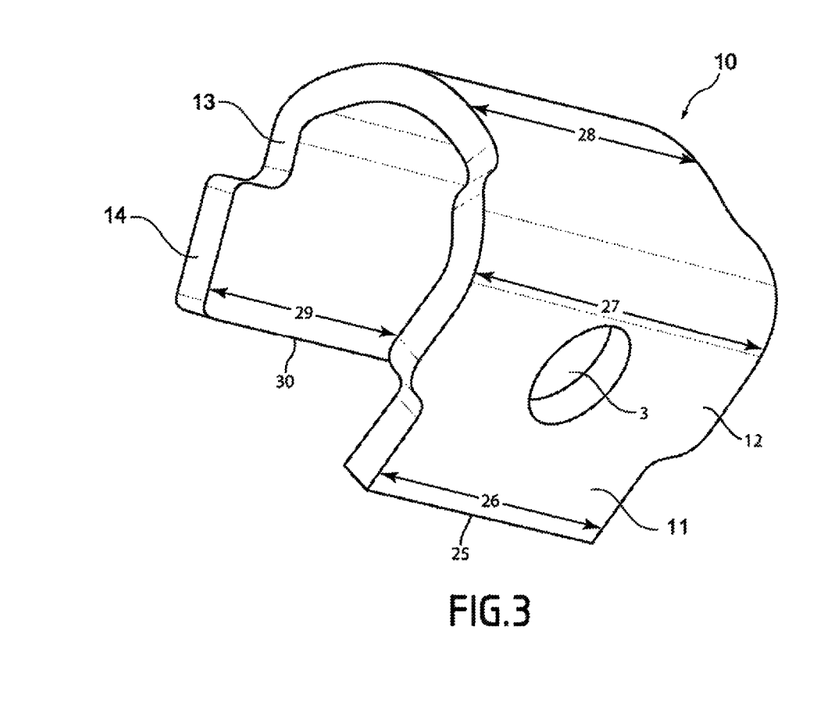
FIG. 3 shows a perspective view of the clip associated with this bracket.

The clip 10, which is shown in isolation in FIG. 3, has elastic properties which enable it to fulfill the functions which will be described below. It is approximately U-shaped, with the arms being, at rest, slightly constricted in the example shown.

In the example shown, the clip 10 is composed of four successive functional parts, two contiguous parts having, in the example shown, different widths that allow them to carry out their respective functions best.

A first part 11, constituting a first terminal end 25 of the clip 10, the first part 11 may be a tongue which has a width 26. The first part 11 functions is to lock the clip 10 in the closed position, since the first part 11 is intended to plunge into the housing 9. The housing 9 being in the wall 4 of the bracket 1 that delimits the groove 2 and is located closest to the base wall 8. The first part 11, when the clip 10 is in the closed position, is held in the housing 9 by the elasticity of the clip 10. Since the housing 9 is delimited around the entire perimeter of its opening, no undesired mesiodistal movement of the clip 10 is possible, and the clip 10 is held firmly in position with no sideways movement being possible.

A second part 12, to which the first part 11 is attached, is intended to close off the groove 2 in the bracket 1 when the clip 10 is in the closed position. Said second part 12 has a width 27 greater than the width 26 of the first part 11, so as to effectively hold the arch wire in the groove 2. It preferably carries gripping means 13 that allow the orthodontist to move the clip 10, by way of a simple rotational movement, between the open position, leaving a free passage to the groove 2 in order to insert the arch wire into the groove 2 or to extract the arch wire from the groove 2, and the closed position in which the groove 2 is blocked from movement of the arch wire into or out of the groove 2. In the example shown, the gripping means 13 is an orifice into which the orthodontist may introduce the end of a tool that forms a lever.

The clip 10 is brought into the "open" position releasing the groove 2 by a rotation voluntarily imposed by the practitioner on the clip 10. Any involuntary rotation of the clip 10 by pressure of the orthodontic arch wire on the second part 12 of the clip 10 in accordance with its natural tendency is rendered impossible by the blocking of the first part 11 by the anterior face A of the housing 9. In addition, the arch wire only applies stresses to the clip 10 in a vestibulolingual direction. This movement of the arch wire in the groove 2 is limited by the possible amplitude of the movement of the first part 11 in the housing 9. Thus, movement of the arch wire in the groove 2 cannot bring about releasing the first part 11 from the housing 9 by rotation of the clip 10 to move the clip 10 into the open position, opening the groove 2. This can only be brought about by a voluntary action by the practitioner who, by rotating the clip 10, disengages the first part 11 from the housing 9.

The increased width of the clip 10 in the region of this second part 12 compared to the first part 11, more effectively holds the arch wire in the groove 2.

A third part 13, having a third width 28, which may be less than the second width 27 of the second part 12, constitutes an elastic junction between, on the one hand, the second part 12 that closes off the groove 2 and, on the other hand, a fourth part 14, having a fourth width 29. The fourth part 14 comprising a second terminal end 30 of the clip 10. This fourth part 14 may be a tab intended to be inserted into the housing 7 formed on the rear wall 6 of the bracket 1. The fourth part 14 and the housing 7 have approximately complementary shapes such that the housing 7 holds the fourth part 14 in the transverse direction OY. The fourth part 14 manages the rotation of the clip 10 during its movements commanded by the orthodontist. In order to carry out its functions best, the fourth width 29 of the fourth part 14 is preferably greater than the third width 28 of the third part 13. The third width 28 of the third part 13 is generally less than the second width 27 of the second part 12 and the fourth width 29 of the fourth part 14, in order to optimize the elasticity of the clip 10 in the region of the third part 13.

The fourth part 14 of the clip 10 thus simultaneously has:
- a function of preventing the partial or complete detachment of the clip 10 and of the bracket 1;
- and a function of guiding the rotation of the clip 10.

Figure 4:
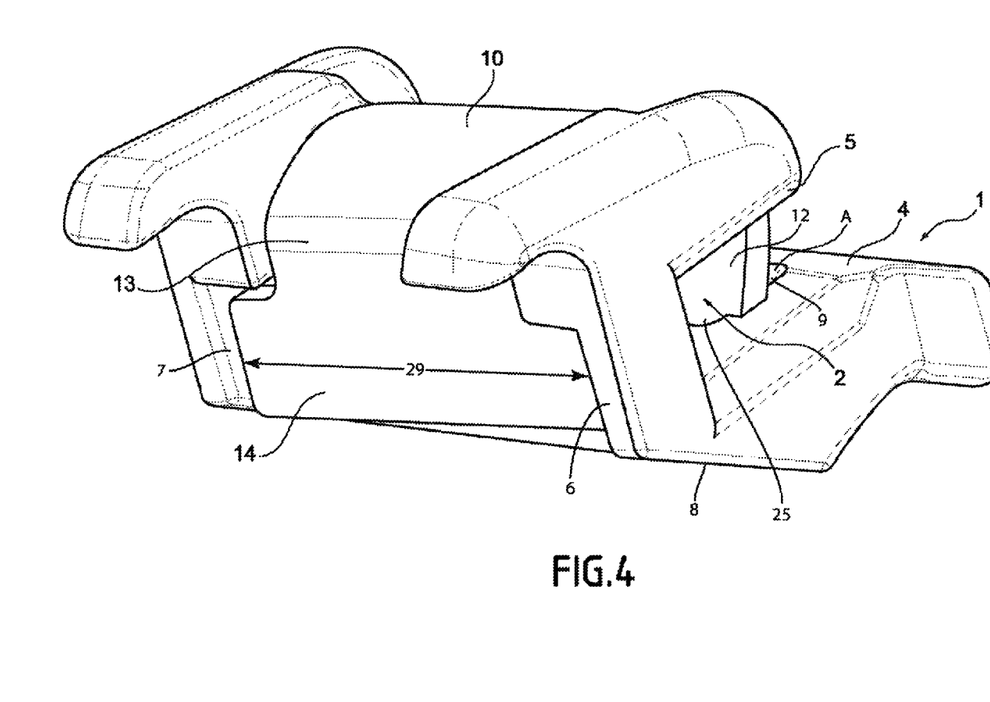
FIG. 4 shows the clip placed on the bracket.

FIG. 4 shows the bracket 1 with the clip 10 fitted to it. The terminal ends 25, 30 of the clip 10 are inserted in their respective housings 9, 7 and the clip 10 overlaps the wall 6 which delimiting the groove 2 one a side furthest away from the base wall 8.

The bracket 1 can be manufactured from any conventional material suitable for this use, such as a biocompatible metal material (stainless steel, titanium, ceramic in particular) and by any conventional method that provides the excellent dimensional precision necessary for self-ligating brackets. Machining or laser cutting are particularly recommended, more than rapid prototyping.

Figure 5:
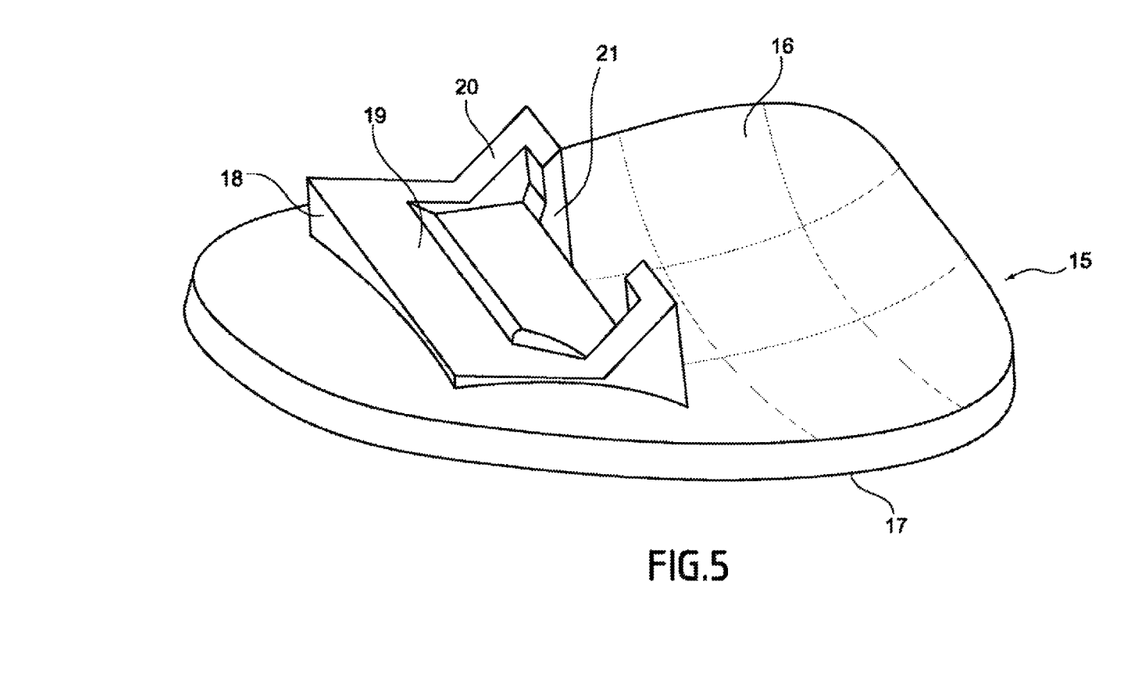
FIGS. 5 and 6 show a perspective view from the front and the rear of the base, on which the bracket is intended to be placed.
Figure 6:
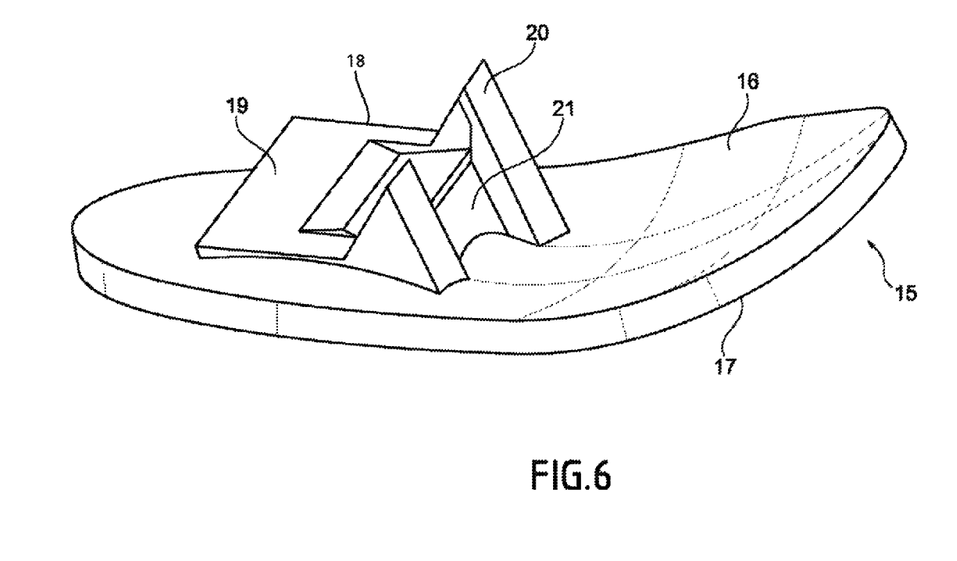

FIGS. 5 and 6 show the outer (upper) face 16 of the base 15 of which the bracket 1 is intended to be fitted. The occlusal (lower) face 17 of the base 15 is intended to be placed on the corresponding tooth of the patient by being conventionally fixed thereto by means of an adhesive material. In the example shown, the upper face 16 of the base 15 carries a support 18 for the bracket 1. This support 18 comprises a planar part 19 and an abutment 20. The planar part 19 can optionally comprise a housing, in which the bracket 1 is intended to be placed. Such a housing promotes the precision of placement of the bracket 1 and contributes to keeping it securely in position. It also reduces the overall thickness of the assembly for one and the same configuration of the bracket 1, thus providing the patient with additional comfort. On that face of the abutment 20 which is intended to face away from the bracket 1, the support 18 also comprises a housing 21 into which the fourth part 14 of the clip 10 is intended to be inserted when the clip 10 is in the position closing off the groove 2.

Figure 7:
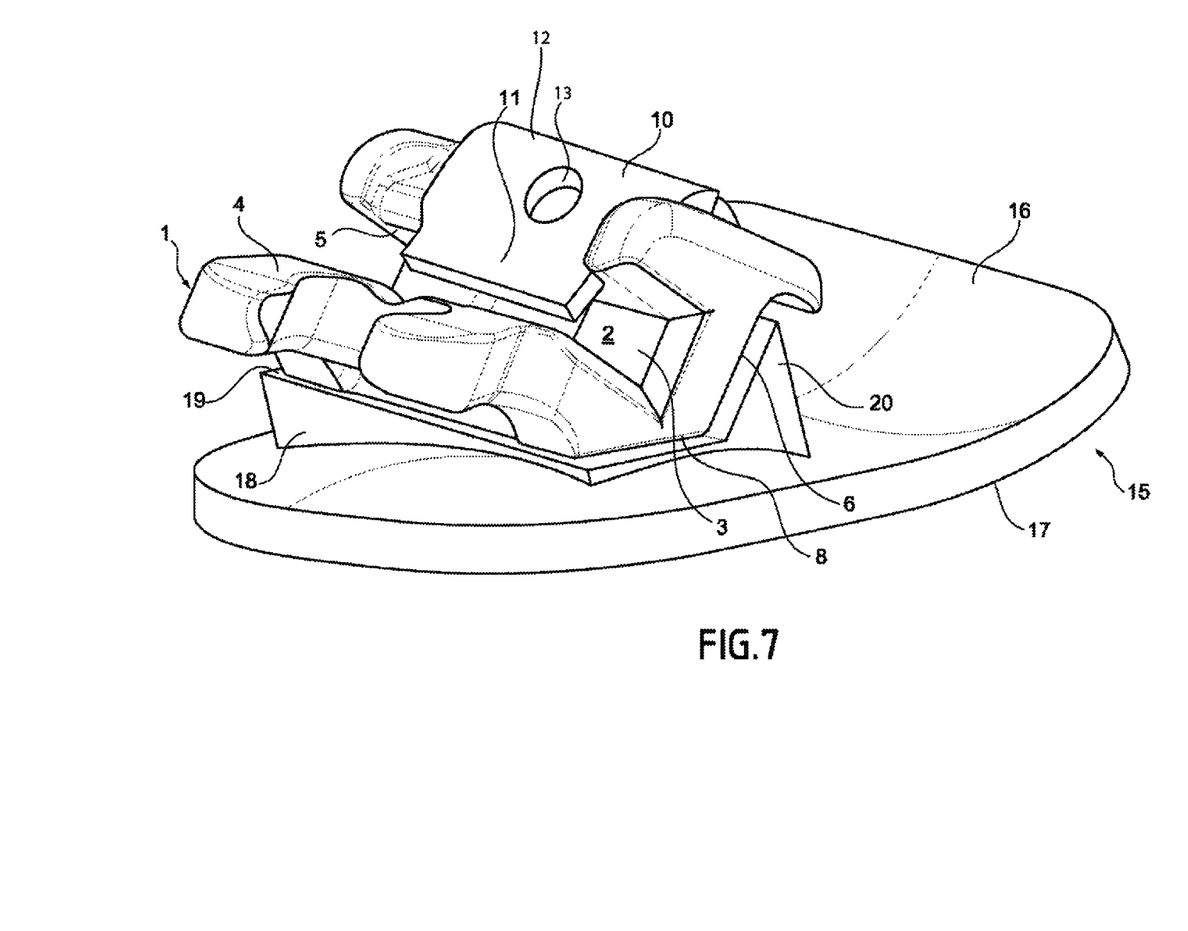
FIG. 7 shows a perspective view from the front of the assembly formed by the bracket, the clip and the base from the preceding figures, with the clip in the open position.

FIG. 7 shows the bracket 1/clip 10/base 15 assembly fitted with the clip 10 in the open position, thus making it possible to insert the orthodontic arch wire into the groove 2 of the bracket 1 or to extract it therefrom. In this position, the lower edge 30 of the fourth part 14 (not visible in FIG. 7) is against the wall of the housing 7 on the rear wall 6 of the bracket 1, the rest of the fourth part 14 is spaced apart from the wall 6 but prevented from moving away therefrom by the walls of the housing 21 of the abutment 20 carried by the base 15.

Figure 8:
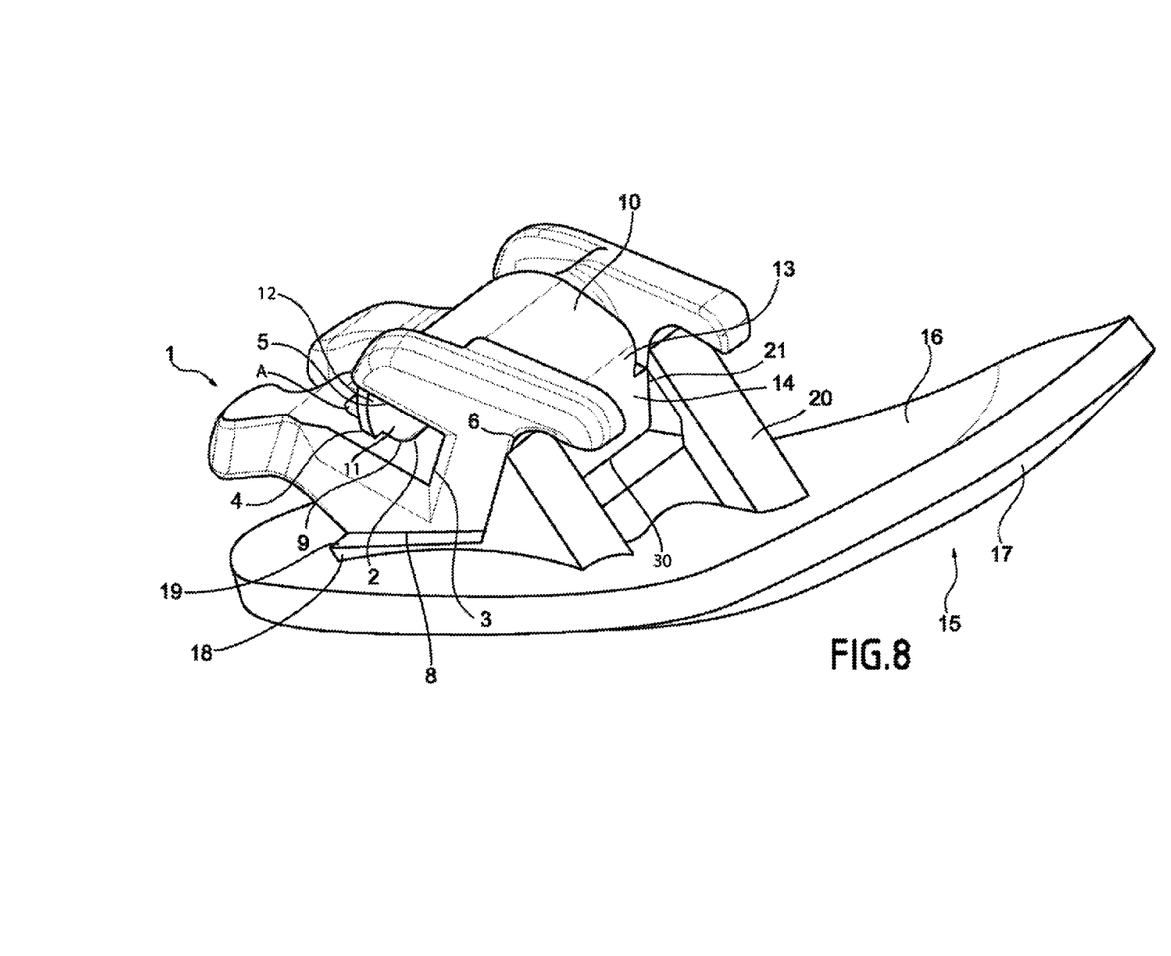
FIG. 8 shows a perspective view from the rear of the assembly formed by the bracket, the clip and the base from the preceding figures, with the clip in the closed position.

FIG. 8 shows a view in the opposite direction to that in FIG. 7 of the bracket 1/clip 10/base 16 assembly fitted with the clip 10 in the closed position, thus blocking the orthodontic arch wire in the groove 2 in the bracket 1. It can be seen that in this position, the fourth part 14 of the clip 10 is pressed against the rear wall 6 of the bracket 1 and is thus contained inside the housing 7. For its part, the first part 11 of the clip 10 has been placed by the orthodontist, by a rotational movement, in the corresponding housing 9 of the bracket 1. This rotational movement is easy and very quick to carry out. In particular, it is not prevented by any build-up of tartar on the assembly because the lever arm produced by the form of the clip 10 and its rotation are sufficient to destroy or detach this build-up, whereas a translational movement, for example along the longitudinal axis OX of the bracket 1, would tend to be considerably hampered by a build-up of tartar on the track of the clip.

The clip 10 has sufficient elasticity to keep the terminal ends 25, 30 of the clip 10 in their respective housings 9, 7. The orthodontic arch wire only being able to exert forces on the clip 10 in the direction of removal of the arch wire from the groove 2 (axis OX) since these forces are channeled by the walls 4, 5 of the groove 2 and thus do not tend to remove the clip 10 from its housings 7, 9.

The configuration of the clip 10 which has been described and represented is only one preferred example, and other configurations would be possible insofar as, in cooperation with the bracket 1, they would allow the latter to fulfill its functions with the advantages that have been cited. In particular, the clip 10 may comprise more or fewer than four functional parts, of different or identical widths.

The invention claimed is:

1. An orthodontic assembly comprising:
a bracket having a longitudinal dimension, a perpendicular dimension and a transverse dimension, wherein in the longitudinal dimension the bracket extends between an outer face and an occlusal face and includes a rear wall on the occlusal face and a groove extends into the bracket from the outer face in the longitudinal dimension, the groove defined by a first wall and a second wall, the first and second walls extend generally in the longitudinal and transverse dimensions, the groove further defined by an end wall that generally extends in the perpendicular and transverse dimensions, a first housing extends into the bracket in the longitudinal dimension from the rear wall; and a clip having a variable width across the entire clip in the transverse dimension and a first arm with a first end and a second arm with a second end, the second end of the clip rotatably secured within the first housing such that the clip is rotatably movable about the second end between an open position wherein the groove is open and a closed position wherein the first arm of the clip occludes the groove;

wherein the variable width is comprised of at least four successive functional parts, a first part, comprising the first end of the clip and having a first width across the entire clip in the transverse dimension, a second part having a second width across the entire clip in the transverse dimension to which the first part is attached, the second width different from the first width, the second part closes off the groove in the bracket when the clip is in the closed position, a third part having a third width across the entire clip in the transverse dimension, the third width different from the second width, and constituting an elastic junction between the second part and a fourth part, the fourth part having a fourth width across the entire clip in the transverse dimension, the fourth width different from the third width, and comprising the second end of the clip, wherein the fourth part is received into the first housing of the bracket and the clip rotates about the second end within the first housing between the open position and the closed position.

2. The assembly as claimed in claim 1, wherein the second wall comprises a second housing extending into the bracket generally in the perpendicular and transverse dimensions, and wherein the first width is less than the second width and when the clip is in the closed position, the first part of the clip is received within the second housing.

3. The assembly as claimed in claim 1, wherein the second width of the second part of the clip extends across the entirety of the groove in the transverse dimension.

4. The assembly as claimed in claim 1, wherein the fourth width of the fourth part of the clip is greater than the third width of the third part of the clip, the fourth width of the fourth part being coextensive with a width of the first housing in the transverse dimension.

5. The assembly as claimed in claim 1, wherein the clip comprises a gripping means enabling the practitioner to move it between said positions.

6. The assembly as claimed in claim 5, wherein said gripping means is an orifice formed on said second part of the clip.

7. The use of an assembly as claimed in claim 1, wherein the orthodontic apparatus is a lingual orthodontic apparatus.

8. The assembly as claimed in claim 1, wherein the orthodontic apparatus is a vestibular orthodontic apparatus.

9. An orthodontic assembly comprising:
a bracket having a longitudinal dimension, a perpendicular dimension and a transverse dimension, wherein in the longitudinal dimension the bracket extends between an outer face and an occlusal face and includes a rear wall on the occlusal face and a groove extends into the bracket from the outer face in the longitudinal dimension, the groove defined by a first wall and a second wall, the first and second walls extend generally in the longitudinal and transverse dimensions, and a first housing extends into the bracket in the longitudinal dimension from the rear wall; and an elastic clip, having a variable width across the entire transverse dimension of the elastic clip at four successive functional parts including a tongue of a first width across the entire clip in the transverse dimension, a closure adjacent the tongue with a second width across the entire clip in the transverse dimension, the second width greater than the first width, an elastic junction adjacent the closure with a third width across the entire clip in the transverse dimension, the third width different from the second width, and a tab adjacent the elastic junction with a fourth width across the entire clip in the transverse dimension, the fourth width different from the third width, the tab comprising an end moveably received within the first housing, wherein the elastic junction elastically connects the closure to the tab;

wherein the elastic clip is pivotable with respect to the bracket about the end of the tab between a closed position wherein the second portion generally occludes the groove, and an open position wherein the groove is generally accessible.

10. The assembly of claim 9, wherein the first width is less than the second width, the third width is less than the second width, and the third width is less than the fourth width.

11. The assembly of claim 9, wherein the second wall further comprises a second housing extending into the bracket from the second wall, wherein the tongue portion is received within the second housing when the clip is in the closed position.

12. The assembly of claim 11, wherein the second wall extends past the first wall in the longitudinal dimension and the second housing extends into the bracket in the transverse and perpendicular dimensions.

13. The assembly of claim 11, wherein the fourth width of the fourth part is coextensive with a width of the first housing in the transverse dimension.

14. A self-ligating bracket comprising:
a bracket having a longitudinal dimension, a perpendicular dimension and a transverse dimension, wherein in the longitudinal dimension the bracket extends between an outer face and an occlusal face and includes a rear wall on the occlusal face and a groove extends into the bracket from the outer face in the longitudinal dimension, the groove defined by a first wall and a second wall, the first and second walls extend generally in the longitudinal and transverse dimensions, the groove further defined by an end wall that generally extends in the perpendicular and transverse dimensions, a first housing extends into the bracket in the longitudinal dimension from the rear wall, and a second housing extends into the bracket from the second wall; and
a clip having a variable width and pivotably movable about the bracket between an open position and a closed position, the variable width comprised of at least a first portion having a first width in the transverse dimension and configured to be secured within the second housing when the clip is in the closed position, a second portion adjacent the first portion and having a second width in the transverse dimension, the second width different from the first width, and configured to occlude the groove when the clip is in the closed position, a third portion adjacent the second portion and having a third width in the transverse dimension, the third width different from the second width, and a fourth portion adjacent the third portion and having a fourth width in the transverse dimension, the fourth width different from the third width, the fourth portion comprising an end of the clip and the fourth portion movably secured within the first housing such that the clip pivots between the open position and the closed position about the end of the fourth portion;

wherein the second housing further comprises an anterior face that engages the first portion of the clip and blocks pivotable movement of the clip between the closed position and the open position when a force is applied to the second portion of the clip in the longitudinal dimension.

15. The self-ligating bracket of claim 14, wherein the bracket further comprises a base wall below the groove in the perpendicular dimension proximate the second wall and further comprising:
a base comprising an outer face and an occlusal face, the occlusal face configured to conform to a surface of a tooth, the outer face further comprising a support which comprises a planar portion and an abutment, a third housing extending into the abutment in the longitudinal dimension, the base wall of the bracket secured to the planar portion and the rear wall of the bracket secured to the abutment such that the first and third housings align to form a combined fourth housing and the fourth portion is movably secured within the fourth housing.

16. The self-ligating bracket of claim 14, wherein the second width of the second portion of the clip extends across the entirety of the groove in the transverse dimension when the clip is in the closed position.

17. The self-ligating bracket of claim 16, wherein the second portion of the clip further extends across the groove in a perpendicular dimension when the clip is in the closed position.

18. The self-ligating bracket of claim 14, wherein the second width is greater than the first width and third width, and the fourth width is greater than the third width.

19. The self-ligating bracket of claim 18, wherein fourth width of the fourth part is coextensive with a width of the first housing in the transverse dimension.

* * * * *